United States Patent [19]

Paschal et al.

[11] 4,210,584
[45] Jul. 1, 1980

[54] VINDESINE SYNTHESIS

[75] Inventors: Gloria C. Paschal, Mooresville; Gerald L. Thompson, Indianapolis, both of Ind.

[73] Assignee: Eli Lilly and Company, Indianapolis, Ind.

[21] Appl. No.: 3,442

[22] Filed: Jan. 15, 1979

[51] Int. Cl.$^2$ .......................................... C07D 519/04
[52] U.S. Cl. .................................. 260/244.4; 546/51; 546/23
[58] Field of Search ...................................... 260/244.4

[56] References Cited

U.S. PATENT DOCUMENTS 2,756,235  7/1956  Ainsworth ............................ 546/69

FOREIGN PATENT DOCUMENTS 2415980  10/1974  Fed. Rep. of Germany .

*Primary Examiner*—Donald G. Daus
*Assistant Examiner*—David E. Wheeler
*Attorney, Agent, or Firm*—James L. Rowe; Arthur R. Whale

[57] ABSTRACT

Vindesine is prepared by converting 4-desacetyl VLB C-3 carboxhydrazide to the corresponding azide with a nitrite such as n-butyl nitrite in THF and then reacting the thus formed azide with triphenylphosphine to yield an intermediate acyl iminophosphorane, which compound is decomposed with acid to yield vindesine of high purity and in good yield.

6 Claims, No Drawings

VINDESINE SYNTHESIS

BACKGROUND OF THE INVENTION

Vindesine (4-desacetyl VLB C-3 carboxamide) has the following structure

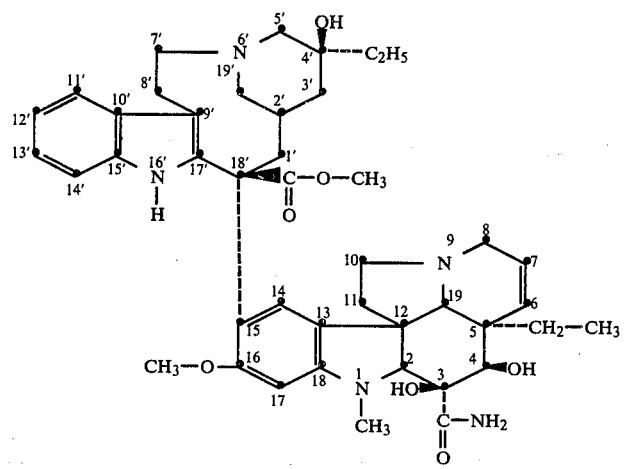

I

Vindesine was first described by Cullinan and Gerzon, Belgian Pat. No. 813,168, as one member of a new group of vinca alkaloid derivatives, the C-3 carboxamides. Methods heretofore utilized for the preparation of vindesine have included: reaction of VLB and ammonia in a sealed tube (partial hydrolysis of the C-4 acetyl group takes place during the reaction and/or work-up); reaction of VLB with hydrazine hydrate to yield 4-desacetyl VLB C-3 carboxhydrazide (with hydrazine, hydrolysis of the C-4 acetyl is virtually complete) followed by reaction with nitrous acid to give the C-3 carboxazide which is in turn reacted with ammonia to yield the C-3 carboxamide; and hydrogenolysis of 4-desacetyl VLB C-3 carboxhydrazide prepared as above with Raney nickel by the procedure of Ainsworth, U.S. Pat. No. 2,756,235, to yield vindesine directly. Each of these procedures suffers from one or more disadvantages. For example, it is very difficult to scale-up a Raney nickel production process and yeilds of desired products differ from batch to batch of Raney nickel. A reliable process suitable for manufacturing vindesine on a commercial scale is clearly needed. Direct reaction of VLB with ammonia yields a mixture of products, etc.

Vindesine is now undergoing extensive clinical trial as an oncolytic agent, particularly for the treatment of leukemia, in the United States and abroad. The compound approachs the activity of vincristine in the treatment of leukemia but with a somewhat different spectrum of side-effects. In addition, certain vincristine-resistant leukemias have been found to be susceptible to vindesine treatment. Finally there is an indication of vindesine activity against both oat-cell and non-oat cell carcinomas of the lung.

It is an object of this invention to provide a commercially feasible synthesis of vindesine which gives highly reproducible yields of the desired product and is accompanied by a minimum number of those by-products which are difficult to remove from vindesine by chromatography.

SUMMARY OF THE INVENTION

In fulfillment of the above and other objects, 4-desacetyl VLB C-3 carboxhydrazide prepared by the method of Cullinan and Gerzon, Belgian Pat. No. 813,168, is reacted with nitrous acid or an organic nitrite ester in acid solution to yield the corresponding azide. The azide is then treated with triphenylphosphine to yield an acyl iminophosphorane, hydrolysis of which with acid yields vindesine directly. The above procedure is more fully exemplified by the following reaction scheme in which only the vindoline (lower) portion of the alkaloid is given, the velbanamine (upper) portion being indicated by a dotted line and "VELB".

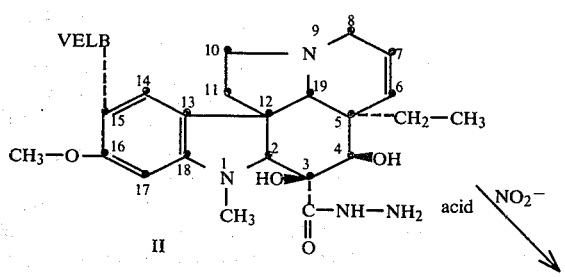

II

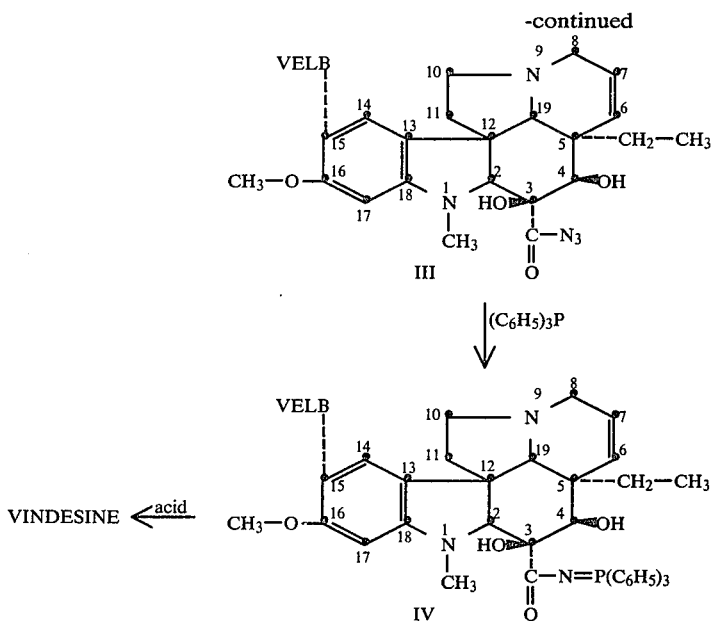

In the above reaction, we have found that either n-butyl nitrite or isoamyl nitrite is the reagent of choice for the conversion of the hydrazide to the azide and that THF (tetrahydrofurane) is the preferred organic solvent for this reaction. Six equivalents of 1 N aqueous hydrochloric acid and 2 equivalents of n-butyl nitrite are necessary to achieve complete conversion of the hydrazide to the azide within a desirably short time span, as for example, five minutes. Longer reaction times result in an increased production of undesirable by-products. Furthermore, the temperature of the aqueous acidic reaction mixture should be kept below about 0° C., also to avoid by-product formation. Lower temperatures cause freezing of the water present. Conversion of the isolated azide to the acyl iminophosphorane is carried out under aprotic conditions by adding triphenylphosphine in an organic solvent in dropwise fashion to a reaction mixture containing 4-desacetyl VLB C-3 carboxazide, preferably in the same solvent. The reaction mixture is allowed to stir at about 0° C. for one hour. The volatile constituents are then removed by evaporation in vacuo, leaving as a residue, the acyl iminophosphorane (IV) plus excess triphenylphosphine. This residue is stable and can be stored. Next, the residue is treated with aqueous acid, thereby hydrolyzing the acyl imino phosphorane to vindesine. Sufficient acid and water are present to solubilize the vindesine as an acid addition salt. The insoluble phosphine and phosphine oxide are removed by extraction with a suitable water-immiscible organic solvent such as methylene dichloride. Vindesine is then isolated and purified using standard procedures. The yield of vindesine from 4-desacetyl VLB C-3 carboxhydrazide is in the range 60 to 80%.

Preferably, however, the above reaction sequence is carried out without isolating any of the intermediate compounds. 4-desacetyl VLB C-3 carboxhydrazide is converted to the azide with an organic nitrite in an acidic aqueous solution with an organic solvent such as THF. Triphenylphosphine, as a solution in the same solvent used in the formation of the azide, is added, and the acyl iminophosphorane is formed as a transient intermediate since the continuing presence of aqueous acid rapidly hydrolyzes that intermediate to vindesine.

All of the 4-desacetyl VLB derivatives, the C-3 carboxhydrazide, carboxazide and carboxamide, are present during the reaction sequence in the form of their acid addition salts. Sufficient water must thus be present at all times to solubilize these acid addition salts.

After the triphenylphosphine has been added, additional aqueous acid is next added to maintain the vindesine in the aqueous phase during the subsequent reaction. Methylene dichloride is then added and the organic phase separated as before. Vindesine is isolated as such by making the acidic aqueous phase alkaline and extracting the now insoluble vindesine free base into an organic solvent. Evaporation of the solvent yields vindesine which can be further purified by high-pressure liquid chromatography or other convenient procedure.

The ability to carry out the above process in a single reaction vessel-a one-pot process-has great commercial appeal.

In the above process, other sources of nitrite than isoamyl nitrite or n-butyl nitrite can be employed as, for example, sodium nitrite, but, as previously stated, we prefer to use n-butyl nitrite or isoamylnitrite in THF for maximum yields.

This invention is further illustrated by the following specific examples.

EXAMPLE 1

Seventy-seven milligrams of 4-desacetyl VLB C-3 carboxhydrazide were dissolved in 2 ml. of 1 N aqueous hydrochloric acid and the resulting solution cooled to about 0° C. 8.4 mg. of sodium nitrite were added and the reaction mixture stirred at about 0° C. for five minutes. Cold saturated aqueous sodium bicarbonate solution was then added and the resulting aqueous mixture extracted with cold methylene dichloride. The methylene dichloride extract was separated and dried over sodium sulfate and the methylene dichloride removed therefrom by evaporation. The residue, comprising 4-desacetyl VLB C-3 carboxazide formed in the above reaction, was dissolved in 7 ml. of THF and an excess of triphenylphosphine in THF added in dropwise fashion.

The reaction mixture was stirred for an hour after the addition of the triphenylphosphine had been completed. An excess of 1 N aqueous hydrochloric acid was added to the THF solution and the reaction stirred at room temperature for about 30 minutes. Thin-layer chromatography indicated that the major product of the reaction was vindesine, with very few by-products being present.

EXAMPLE 2

76.8 Milligrams of 4-desacetyl VLB C-3 carboxyhydrazide were dissolved in 1 ml. of THF and 1 ml. of glacial acetic acid. The reaction mixture was cooled to about 0° C. and 0.2 ml. of a ten percent solution (v/v) of n-butyl nitrite in THF was added in dropwise fashion. This reaction mixture was stirred at about 0° for about five minutes. 262 mg. of triphenylphosphine in 2 ml. of THF were next added in dropwise fashion and the resulting reaction mixture stirred at 0° C. for about 30 minutes after the addition of the triphenylphosphine had been completed. TLC (ethyl acetate/methylene dichloride/methanol system) indicated that, while vindesine had been prepared, the conversion was only about 20 percent and that the reaction mixture contained both starting material plus 1 or 2 unknown substances.

EXAMPLE 3

One gram of 4-desacetyl VLB C-3 hydrazide was dissolved in 25 ml. of THF and the resulting solution cooled to about 0° C. 7.8 ml of 1 N aqueous hydrochloric acid were added followed by 2.6 ml. of a ten percent (v/v) n-butyl nitrite solution in THF (2 equivalents of n-butyl nitrite). The reaction was stirred at 0° C. for five minutes. Next, 3.4 g. of triphenylphosphine in 25 ml. of THF (10 equivalents) were added to the solution in dropwise fashion and the reaction mixture stirred at 0° C. for about one hour. The reaction mixture was then warmed to room temperature and diluted with 1 N aqueous hydrochloric acid. The reaction mixture was extracted three times with equivalent volumes of methylene dichloride. The solution was then made basic by the addition of 5 N aqueous sodium hydroxide and the basic solution extracted four times with equal volumes of methylene dichloride. The organic extracts were combined and the combined extracts dried. Evaporation of the organic solvent yielded 946 mg. of a residue comprising vindesine. Yield of vindesine by HPLC was at least 63.7 percent of total solids. Yield of vindesine based on 4-desacetyl-VLB C-3 carboxhydrazide starting material was 61.6%.

EXAMPLE 4

1.973 Grams of 4-desacetyl VLB C-3 carboxhydrazide were dissolved in 50 ml. of THF and the resulting solution cooled to about 0° C. with stirring under a nitrogen atmosphere. 15.6 ml. of 1 N aqueous hydrochloric acid were added followed by 5.2 ml. of 10 percent (v/v) n-butyl nitrite in THF in a single portion. The reaction mixture was stirred at 0° C. for five minutes after which time a solution of 6.8 g. of triphenylphosphine in 50 ml. of THF was added in dropwise fashion. After addition of the triphenylphosphine had been completed, the reaction was stirred at 0° C. for about one hour and then diluted with 25 ml. of water. The THF was evaporated in vacuo. The remaining aqueous suspension was diluted with 1 N aqueous hydrochloric acid and the acidic solution extracted twice with methylene dichloride. The pH of the acidic solution was adjusted to about 10 with 14 N aqueous ammonium hydroxide and the resulting alkaline solution extracted three times with methylene dichloride. The organic extracts were combined and the combined extracts dried. Evaporation of the solvents yielded 1.95 g. of crude vindesine. Purification by HPLC followed by recrystallization of the free base provided a 74.6% yield of pure vindesine.

We claim:

1. The process which comprises the steps of reacting 4-desacetyl VLB C-3 carboxhydrazide with a nitrite in the presence of acid in an inert solvent to form 4-desacetyl VLB C-3 carboxazide, reacting said carboxazide with triphenylphosphine to yield 4-desacetyl VLB C-3 N-(triphenylphosphoranyl)carboximide and then reacting said iminophosphorane of 4-desacetyl VLB carboxylic acid with acid to yield vindesine.

2. A process according to claim 1 in which an alkyl nitrite in tetrahydrofuran is the nitriting reagent.

3. The process which comprises reacting 4-desacetyl VLB C-3 carboxazide with triphenylphosphine to form 4-desacetyl VLB C-3 N-(triphenylphosphoranyl)carboximide and then decomposing said iminophosphorane of 4-desacetyl VLB carboxylic acid with acid to yield vindesine.

4. A process according to claim 2 in which isoamylnitrite is the alkyl nitrite.

5. A process according to claim 2 in which n-butyl nitrite is the alkyl nitrite.

6. A compound of the formula

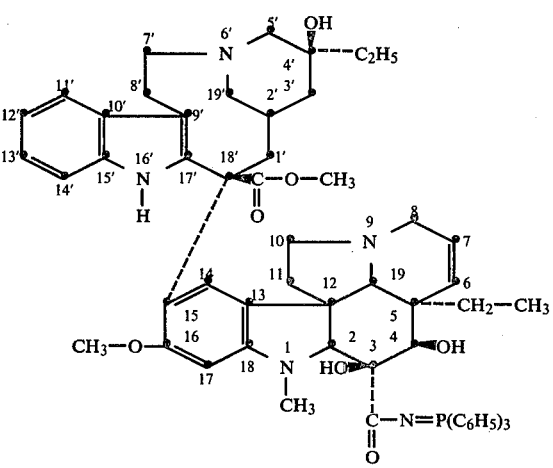

* * * * *